United States Patent [19]
Glockler

[11] Patent Number: 5,912,775
[45] Date of Patent: Jun. 15, 1999

[54] METHOD AND APPARATUS FOR TEMPORAL AND SPATIAL BEAM INTEGRATION

[75] Inventor: Herrmann J Glockler, Cupertino, Calif.

[73] Assignee: VISX, Incorporated, Santa Clara, Calif.

[21] Appl. No.: 08/845,510

[22] Filed: Apr. 24, 1997

Related U.S. Application Data

[62] Division of application No. 08/368,799, Jan. 4, 1995, Pat. No. 5,646,791.

[51] Int. Cl.[6] .................. G02B 5/04; G02B 27/10; G02B 26/00; G02B 26/08
[52] U.S. Cl. .................. 359/831; 359/837; 359/618; 359/623; 359/238; 359/236; 359/298
[58] Field of Search .................. 359/831, 837, 359/618, 623, 625, 632, 639, 640, 238, 236, 298, 233, 235; 606/17, 18, 5

[56] References Cited

U.S. PATENT DOCUMENTS

| | | | |
|---|---|---|---|
| 3,877,777 | 4/1975 | Glenn, Jr. | 359/202 |
| 3,924,937 | 12/1975 | Munroe et al. | 359/202 |
| 4,393,408 | 7/1983 | Beck et al. | 348/202 |
| 4,997,250 | 3/1991 | Ortiz, Jr. | 385/33 |
| 5,013,311 | 5/1991 | Nouri | 606/4 |
| 5,016,149 | 5/1991 | Tanaka et al. | 362/259 |
| 5,074,859 | 12/1991 | Koziol | 606/5 |
| 5,095,386 | 3/1992 | Scheibengraber | 359/668 |
| 5,152,759 | 10/1992 | Parel et al. | 606/5 |
| 5,166,508 | 11/1992 | Davis et al. | 250/201.9 |
| 5,194,980 | 3/1993 | Roddy | 359/204 |
| 5,281,211 | 1/1994 | Parel et alk. | 606/5 |
| 5,284,477 | 2/1994 | Hanna et al. | 606/5 |
| 5,285,308 | 2/1994 | Jenkins et al. | 359/260 |
| 5,392,149 | 2/1995 | Boardman et al. | 359/216 |

FOREIGN PATENT DOCUMENTS

| | | | |
|---|---|---|---|
| 0 050 546 | 10/1981 | European Pat. Off. | |
| 0 152 686 A1 | 8/1985 | European Pat. Off. | A61B 17/36 |
| 0 296 982 A1 | 12/1988 | European Pat. Off. | A61F 9/00 |
| 0 536 951 | 10/1992 | European Pat. Off. | |
| 0 628 298 A1 | 12/1994 | European Pat. Off. | A61F 9/00 |
| 4 103 615 | 2/1991 | Germany | |

OTHER PUBLICATIONS

Description of 2020B Optical Schematic (0019–5720).
Schematic Diagram Drawing No. 00195720 dated Oct. 16, 1987.

*Primary Examiner*—Cassandra Spyrou
*Assistant Examiner*—Mohammad Y. Sikder
*Attorney, Agent, or Firm*—Townsend and Townsend and Crew LLP

[57] ABSTRACT

A method and apparatus for providing sequential temporal and spatial integration of a collimated non-symmetrical excimer laser beam to optimize the temporal and spatial characteristics of the beam. The temporal integrator comprises a pair of cylindrical lenses spaced along the beam axis by a distance substantially equal to the sum of the focal length of both lenses, and a motor mechanism for rotating the two spaced cylindrical lenses about the beam axis. The spatial beam integrator includes a plurality of prisms distributed about a hollow center, the outlet face of each prism being angled with respect to the body axis of the spatial beam integrator so that portions of the laser beam passing through a given prism are refracted towards the center upon emergence from the outlet face. The spatial beam integrator is preferably rotated about the beam axis at twice the rotation rate of the cylindrical lenses so that the rotated beam emerging from the temporal beam integrator is stationary with respect to the spatial beam integrator. Alternatively, the spatial beam integrator may be rotated at the same rate as the cylindrical lenses, or may be maintained stationary, i.e., not rotated at all.

11 Claims, 5 Drawing Sheets

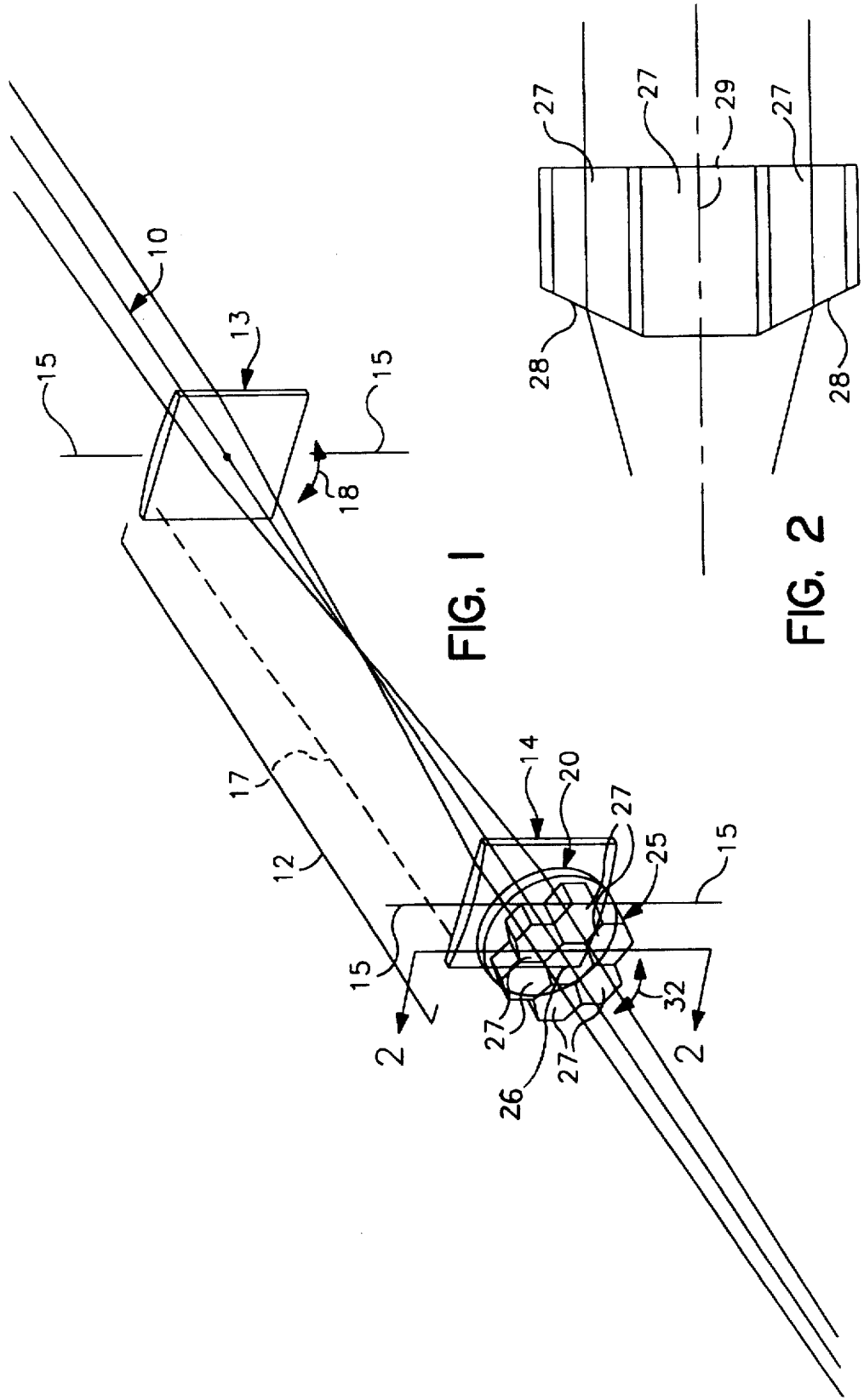

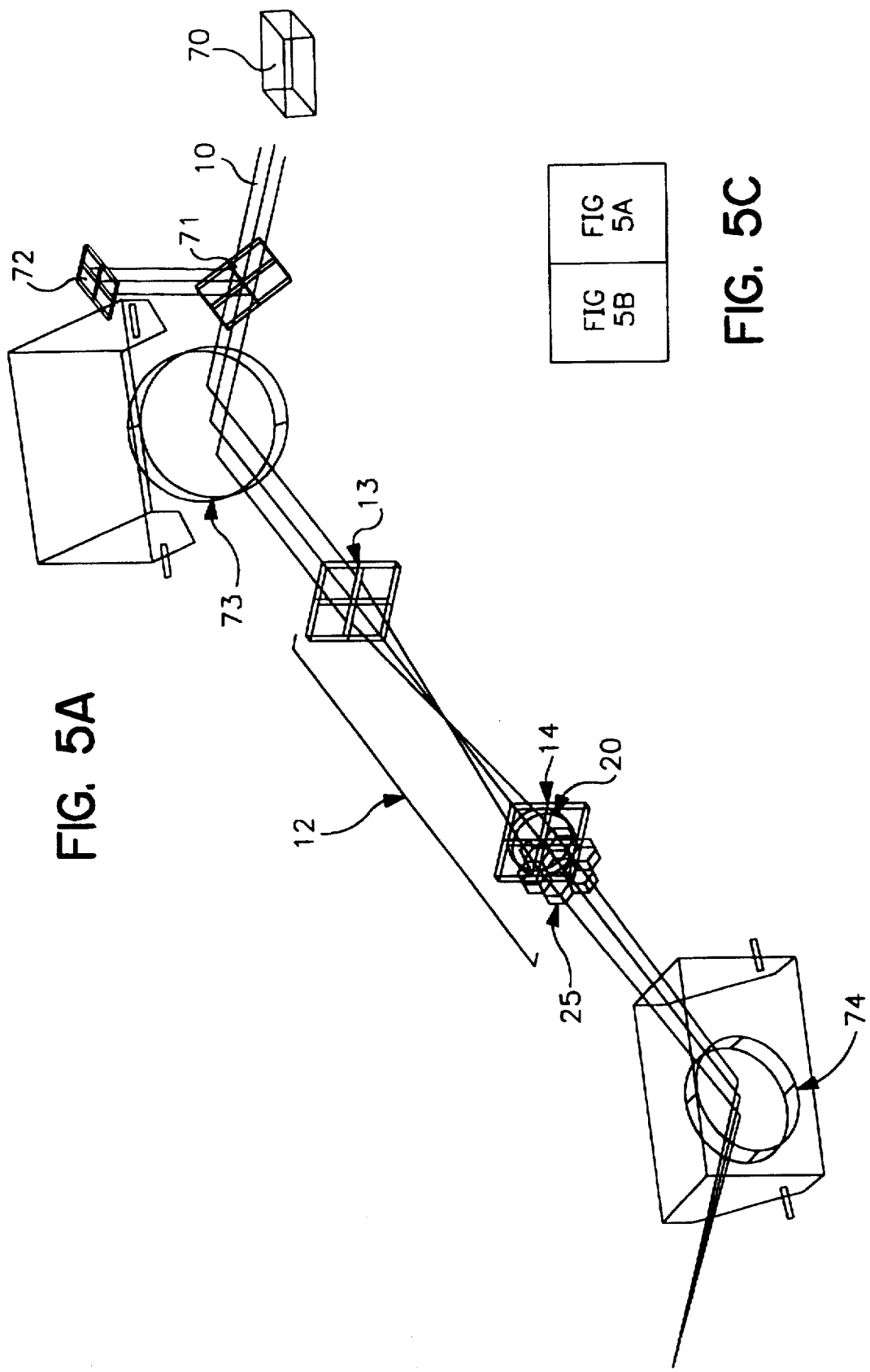

METHOD AND APPARATUS FOR TEMPORAL AND SPATIAL BEAM INTEGRATION

This application is a division of application Ser. No. 08/368,799 filed Jan. 4, 1995 now U.S. Pat. No. 5,646,791.

BACKGROUND OF THE INVENTION

This invention relates to optical beam delivery systems in general, and to optical beam delivery systems used with laser beams to optimize the temporal and spatial characteristics thereof.

Optical beam delivery systems are known which are used to improve the temporal and spatial characteristics of collimated beams of radiation with non-symmetrical energy profile cross sections, such as excimer laser beams. For example, in the Visx Twenty/Twenty Excimer Laser System developed by Visx Incorporated of Santa Clara, Calif., a collimated laser beam used for photorefractive keratectomy (PRK) and phototherapeutic keratectomy (PTK) is delivered to the plane of surgery by means of an optical beam delivery system which provides both spatial and temporal integration for an excimer laser beam. In this system, a collimated laser beam is first passed through a stationary spatial beam integrator comprising a plurality of prisms, which are preferably hexagonal in shape, distributed about an optical center in the form of a similar hollow space, one face of each prism being angled with respect to the central axis so that portions of a laser beam passing through each prism are refracted toward the central axis of the prism assembly. After passing through the spatial beam integrator, the laser beam is next transmitted through a temporal beam integrator comprising a dove prism which is rotated about the longitudinal optical axis in order to rotate the beam. The beam emerging from the temporal beam integrator is then directed through a variable diameter aperture and delivered to the surgical plane by means of appropriate mirrors and lenses.

While highly effective in providing spatial and temporal integration to a collimated laser beam, this arrangement is extremely sensitive to the placement of the dove prism along the optical axis of the beam delivery system. In particular, any slight misalignment of the dove prism results in a multiplication of the angular error by a factor of 2. Since any angular deviations radially displace the overlapping beam relative to the aperture, thereby affecting symmetry of the beam at the treatment site, extreme care must be taken in initially aligning the dove prism with respect to the beam axis and frequent periodic alignment checks must be made to ensure that the initial alignment has not been disturbed. Efforts to provide a spatial and temporal beam integration technique devoid of this disadvantage have not met with success to date.

SUMMARY OF THE INVENTION

The invention comprises a technique for temporally and spatially integrating a collimated laser beam which is relatively easy to initially align with respect to the beam axis, and which is relatively inert and insensitive to angular misalignment of the optical elements which perform the temporal beam integration.

From a process standpoint, the invention comprises a method of processing a collimated laser beam to improve the spatial and temporal characteristics thereof, the method including the steps of first passing the collimated beam through a temporal beam integrator to rotate the beam about the axis thereof at a predetermined rate, and then passing the rotating beam emerging from the temporal beam integrator through a spatial beam integrator to effect spatial integration thereof. The step of passing the collimated beam through a temporal beam integrator preferably includes the steps of positioning a pair of cylindrical lenses arranged in spaced relationship along the axis of the collimated beam, and rotating the pair of cylindrical lenses in unison about the beam axis. The effect of this temporal integrator mechanism is a rotation of the laser beam at a rotational speed of twice the speed of rotation of the cylinder lens pair. In the preferred embodiment, the cylindrical lenses are substantially identical. In one embodiment, the spatial beam integrator is rotated about the beam axis at an angular speed greater than the speed of rotation of the cylindrical lenses, preferably at a speed which is twice the rate of rotation of the cylindrical lenses so that the follow-on spatial beam integrator is relatively stationary with respect to the rotating beam emerging from the cylindrical lenses. In another embodiment, the angular speed of rotation of the spatial beam integrator is made equal to the speed of rotation of the cylindrical lenses. In still another embodiment, the spatial beam integrator is maintained stationary, i.e., not rotated at all.

The first embodiment of the method preferably includes the initial step of rotating the spatial beam integrator about the beam axis before commencing rotation of the temporal beam integrator in order to initially optimize the spatial characteristics of the collimated beam transmitted through the spatial beam integrator.

From an apparatus standpoint, the invention comprises a laser beam delivery apparatus for temporally and spatially integrating a collimated laser beam, the beam delivery apparatus including a pair of cylindrical lenses arranged in spaced relationship along the axis of the collimated laser beam, with the cylinder axes of the cylindrical lenses being substantially aligned. The cylindrical lenses are preferably spaced along the beam axes by an amount substantially equal to the sum of the focal distance of each cylindrical lens. A spatial beam integrator is positioned in the path of the beam emerging from the cylindrical lenses.

In the preferred embodiment, two cylindrical lenses of equal refractive power, with their axes aligned and their separation equal to the sum of their focal distances, are installed in the path of the laser beam. This arrangement provide a substantially equally formed, but rotating, laser beam at the exit of the integrator.

In other embodiments, two cylindrical lenses of unequal refractive power, with their axes aligned and their separation equal to the sum of their focal distances, are installed into the laser beam. This arrangement provides an increased or reduced, but equally rotating, laser beam at the exit of the integrator. The size of the laser beam exiting from this integrator will be affected in width and height by the inverse of the ratio of the first and second integrator lenses and the sine or cosine function of the angle of the first lens to the angle of the laser beam entering such integrator.

The temporal integrator apparatus includes first means for rotating the cylindrical lenses about the beam axes in unison so that a beam passing through the pair of cylindrical lenses is rotated about the beam axis at twice the rotational speed of the lenses. In the preferred embodiment of the invention, the apparatus includes means for providing relative rotation between the spatial beam integrator and the pair of cylindrical lenses. The providing means preferably includes second means for rotating the spatial beam integrator relative to the cylindrical lenses, and means for providing synchronous

3 motion between the first and second rotating means. The angular speed of the spatial beam integrator is preferably set to be a multiple, preferably 2, of the angular speed of rotation of the cylindrical lenses.

The spatial beam integrator preferably comprises a plurality of hexagonal prisms distributed about a center, with each prism having a light outlet face for refracting an emerging portion of the collimated beam towards the center of the prism assembly, each light outlet face being preferably positioned at an angle with respect to a body axis passing through the center of the spatial beam integrator. The center may comprise either a hollow space or an optical element such as a prism having a flat light outlet face.

The apparatus further preferably includes means for permitting initial relative rotation between the spatial beam integrator and the cylindrical lenses in order to optimize the spatial characteristics of the collimated beam passing therethrough. The invention further may include an expanding lens, preferably a spherical lens, positioned in the path of the beam emerging from the downstream one of the pair of cylindrical lenses, preferably between that lens and the spatial beam integrator.

The first means for rotating the cylindrical lenses about the beam axis preferably includes a housing for mounting the cylindrical lenses in proper alignment, a motor for generating mechanical motion, and means for transferring the mechanical motion to the housing. The transferring means preferably comprises a driving gear coupled to the motor and a driven gear coupled to the housing and engagable with the driving gear. The means for providing relative rotation between the spatial beam integrator and the cylindrical lenses preferably comprises a second housing for mounting the spatial beam integrator, a motor for generating mechanical motion, and means for transferring the mechanical motion to the second housing, the transferring means preferably comprising a driving gear coupled to the motor and a driven gear coupled to the housing and engagable with the driving gear. The motor is preferably a single motor shared between the first rotating means and the providing means.

In an alternate embodiment of the invention, the spatial beam integrator is rotated at the same rate as the cylindrical lenses. In another alternate embodiment, the spatial beam integrator is fixed and the cylindrical lenses are rotated. In both of the alternate embodiments, the angular position of the rotated beam with respect to the spatial beam integrator varies with respect to time; while in the preferred embodiment, the angular position of the rotated beam is fixed with respect to the spatial beam integrator.

The invention provides both spatial and temporal integration for a collimated laser beam and is substantially less sensitive to misalignment of the temporal beam integrator with respect to the beam axis. In particular, any off axis misalignment results in multiplication by a factor of approximately 0.5 times the offset, due to the use of the refraction principle of the cylindrical lenses, which compares favorably to the multiplication factor of 2 encountered with temporal beam integrators employing dove prisms.

For a fuller understanding of the nature and advantages of the invention, reference should be had to the ensuing detailed description taken in conjunction with the accompanying drawings.

BRIEF DESCRIPTION OF THE DRAWINGS

FIG. 1 is a schematic diagram of a portion of a laser beam optical delivery system incorporating the invention;

4

Figure 3:
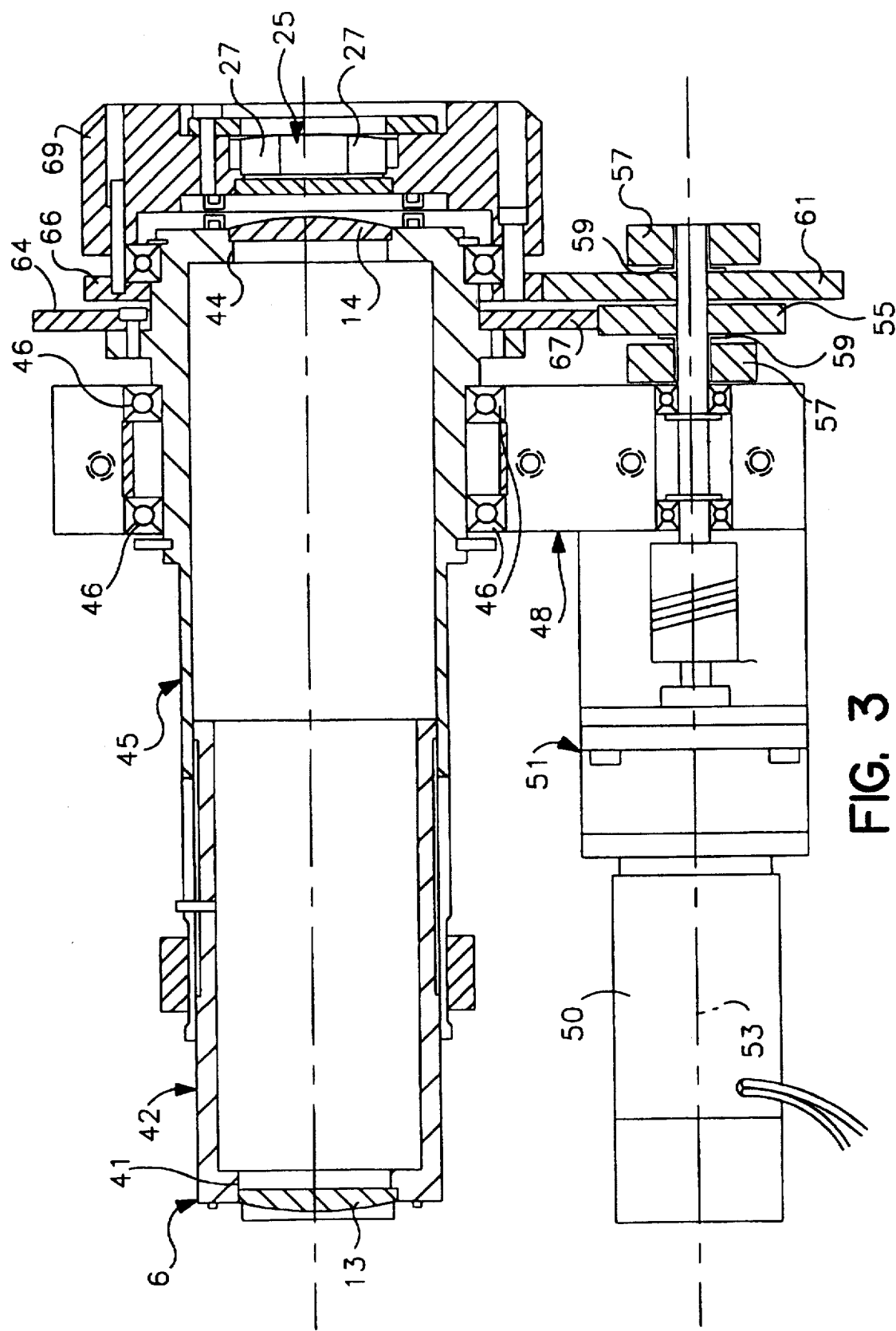
Figure 4:
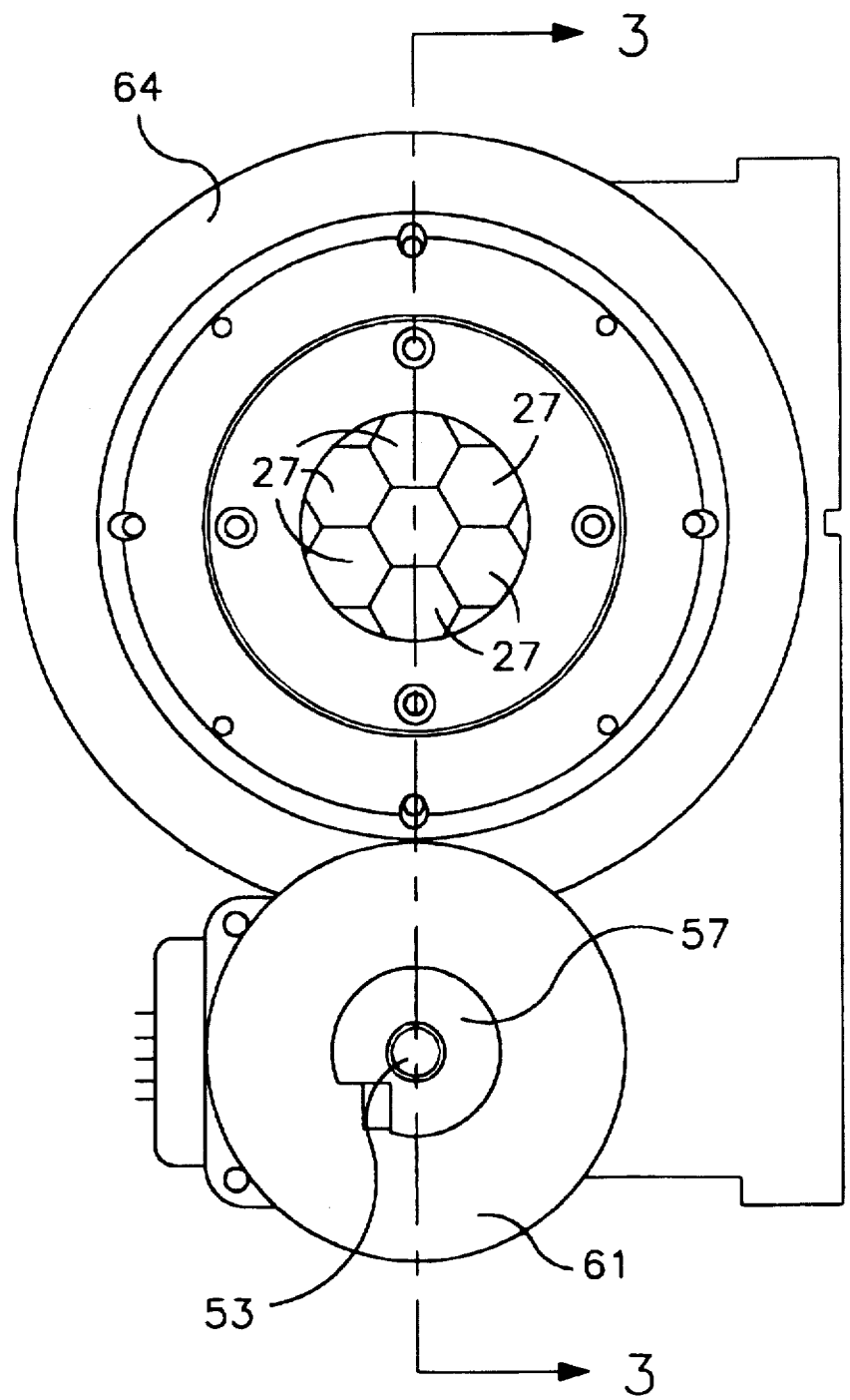
Figure 5B:
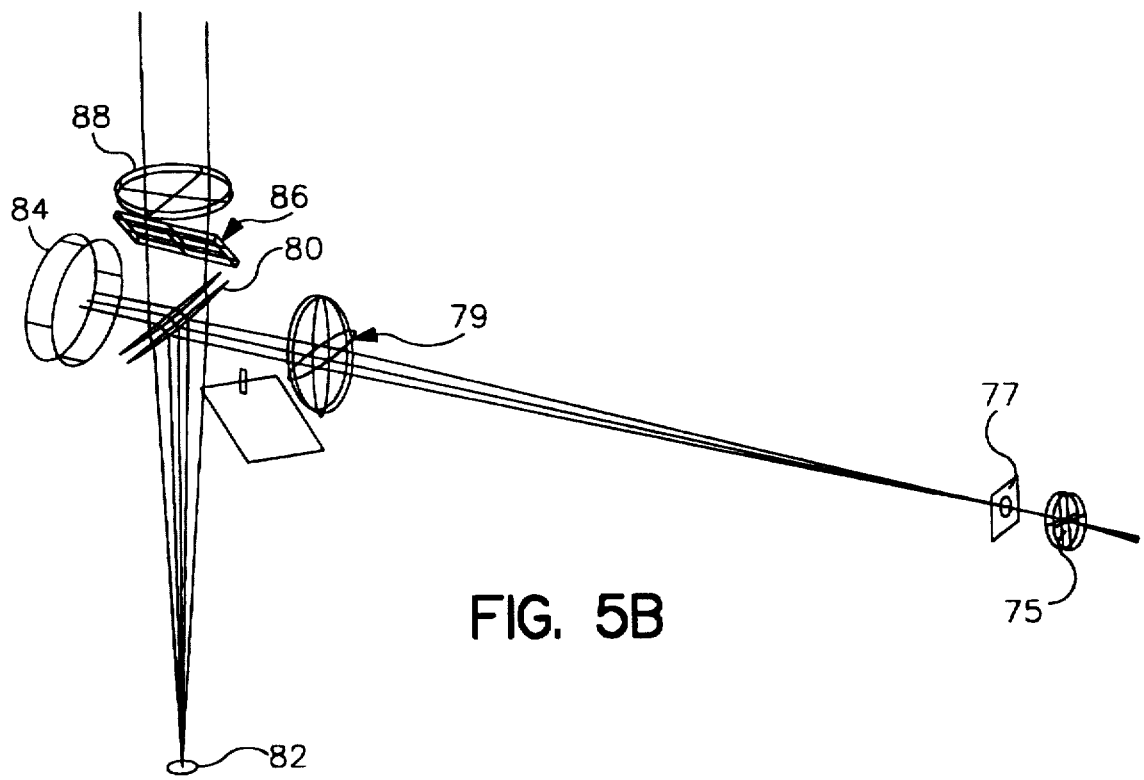

FIG. 2 is a schematic sectional view taken along lines 2—2 of FIG. 1 of a portion of the spatial beam integrator;

FIG. 3 is a sectional view of a preferred embodiment of the invention taken along lines 3—3 of FIG. 4;

FIG. 4 is an end view of the preferred embodiment of the invention;

FIGS. 5A and 5B together constitute a schematic diagram of a laser beam optical delivery system incorporating the invention; and FIG. 5C illustrates the relative orientation of FIGS. 5A and 5B.

Figure 6:
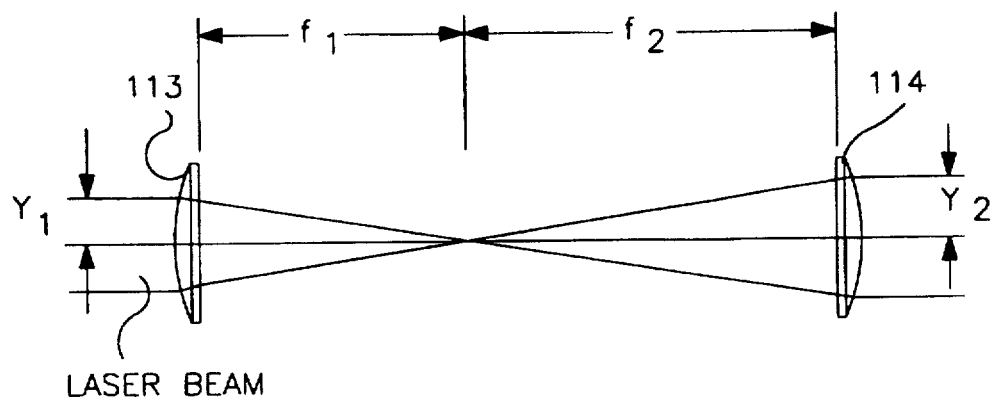

FIG. 6 is a schematic diagram of a temporal beam integrator using two cylindrical lenses of different focal length.

DETAILED DESCRIPTION OF THE PREFERRED EMBODIMENTS

Turning now to the drawings, FIG. 1 illustrates in schematic form a laser beam delivery apparatus according to the invention. As seen in this figure, a collimated beam 10 from a laser source (not shown) is directed onto the inlet face of a temporal beam integrator generally designated with reference numeral 12. In the preferred embodiment of FIG. 1, temporal beam integrator 12 includes a pair of substantially identical cylindrical lenses 13, 14 each arranged in the path of beam 10 and spaced along the beam axis by a distance equal to the sum of the focal distances of the lenses. The cylindrical axes 15 of each of the lenses 13, 14 are aligned with respect to each other, and each lens is arranged with the flat face normal to the beam axis, with the optical center of each lens 13, 14 coincident with the beam axis. The convex cylindrical surface of lens 13 provides the inlet face for temporal beam integrator 12, while the convex face of cylindrical lens 14 forms the outlet face of the temporal beam integrator.

As suggested by broken line 17, cylindrical lenses 13, 14 are mechanically linked, and as suggested by circular arrow 18, cylindrical lenses 13 and 14 are mounted for synchronous rotation about the beam axis. When a beam 10 passes through temporal beam integrator 12 as the lenses 13, 14 are rotated in unison, the rotated beam emerging from the outlet face of lens 14 is rotated twice for each complete revolution of the lens pair 13, 14.

An optional beam expanding lens 20 is positioned in the path of the rotated beam emerging from the temporal beam integrator 12 and is used to expand the beam size in those applications requiring such beam expansion.

A spatial beam integrator generally designated with reference numeral 25 is located in the path of the rotating beam emerging from temporal beam integrator 12 (and optionally emerging from the optional beam expander lens 20). Spatial beam integrator 25 comprises a close packed array of hexagonal prisms 27 clustered about the center of spatial beam integrator 25. As shown in FIG. 2, the outlet face 28 of each of the prisms 27 is angled with respect to the central axis 29 of the spatial beam integrator. As a consequence, that portion of the rotated laser beam passing through each prism is refracted towards the central axis upon emergence from the outlet face 28. The spatially integrated beam emerging from spatial beam integrator 25 is transmitted to follow on optical elements and to the destination site or plane.

As suggested by curved arrow 32, spatial beam integrator 25 may be mounted for rotational movement about the beam axis. In the preferred embodiment, spatial beam integrator 25 is mounted for rotation in the same angular direction as temporal beam integrator 12, but at twice the rotational rate of the temporal beam integrator 12. Thus, the rotated beam emerging from the temporal beam integrator 12 has a fixed angular orientation with respect to spatial beam integrator 25 (since the beam is rotated by a factor of 2 in passing through the two cylindrical lenses 13, 14). In this embodiment, the angular orientation of spatial beam integrator 25 is initially adjusted with respect to the angular orientation of temporal beam integrator 12 with integrator 12 stationary in order to determine the angular position of spatial beam integrator 25 relative to beam 10 which affords the optimum spatial characteristics, i.e., smoothness, profile and homogeneity. Once this orientation has been determined, the relative angular positions of temporal beam integrator 12 and spatial beam integrator 25 are controlled during rotation of these two units such that this optimum angular orientation between the beam 10 and the spatial beam integrator is maintained constant. In this way, the spatial beam integration is optimized.

In a first alternate embodiment of the invention, spatial beam integrator 25 is simply locked to temporal beam integrator 12 and rotated in unison therewith. In still another alternate embodiment, the angular position of the spatial beam integrator 25 is simply fixed and only the temporal beam integrator 12 is rotated. In both of these alternate embodiments, the rotated beam emerging from temporal beam integrator 12 also rotates with respect to spatial beam integrator 25. As a consequence, the initial angular alignment of spatial beam integrator 25 with respect to temporal beam integrator 12 is unnecessary.

FIGS. 3 and 4 illustrate a preferred embodiment of the apparatus for mounting cylindrical lenses 13, 14 and spatial beam integrator prisms 27, and for rotating prisms 27 relative to lenses 13, 14. As seen in these figures, cylindrical lens 13 is mounted in an aperture 41 of a hollow, generally cylindrical member 42. Cylindrical lens 14 is mounted in an aperture 44 in a second generally cylindrical member 45. Member 42 has an outer diameter sized to provide a translatable sliding fit within the inner diameter of member 45 so that the axial separation distance between lenses 13 and 14 may be adjusted.

Mounting member 45 is rotatably mounted by means of bearings 46 to a support member 48. Support member 48 also carries a drive motor 50, a motor transmission mechanism 51 and an output shaft 53. A first driving gear 55 is mounted on shaft 53 and held in place by a friction clamp 57 which is received about a friction flange 59 attached to one face of driving gear 55. A second driving gear 61 is also mounted on shaft 53 by means of a friction clamp 57 and flange 59.

Driving gear 55 is enmeshed with a first driven gear 64 which is secured to housing member 45. Driving gear 61 is engaged with a second driven gear 66 which is secured to a mounting head 69 for spatial beam integrator prisms 27.

In use, cylindrical lenses 13, 14 are arranged within their respective apertures in members 42, 45 with their cylindrical axes aligned, and the separation distance along the beam axis is adjusted until lenses 13, 14 are separated by a distance equal to the sum of the focal distances of both lenses. Next, the array of hexagonal prisms 27 is mounted in member 69, and this assembly is attached to driven gear 66. This assembly is now aligned with the axis of the laser beam (indicated by the phantom line in FIG. 3), after which the laser beam profile is examined while rotating mounting heady 69. Once the optimum relative angular position between the beam and the prisms 27 is attained driving gear 61 is locked to shaft 53 by means of clamp 57 and 59, and driving gear 55 is likewise locked to shaft 53 (unless this step was already done prior to the initial rotational adjustment of mounting head 69). The apparatus is now aligned and ready for use.

In use, motor 50 is operated by appropriate control signals to rotate driving gears 55, 61, and thus rotate housing members 42, 45 in bearings 46 and prisms 27. The relative rates of rotation of the lenses 13, 14 with respect to the prisms 27 are governed by the gear ratios of gears 55, 61, 64 and 66. As will be appreciated by those skilled in the art, these relative rates of rotation can be changed by simply using gears with different ratios, as dictated by the requirements of any particular application.

FIGS. 5A and 5B illustrate the application of the invention to an ophthalmological laser surgery system. FIG. 5C illustrates the relative orientation for FIGS. 5A and 5B. As seen in these figures, a collimated beam 10 from a suitable laser source 70, such as an excimer laser beam source for generating a laser beam in the far ultraviolet range with a wavelength of 193 nanometers, is directed to a beam splitter 71. Part of the beam is reflected onto an energy detector 72; the remaining portion is transmitted through the beam splitter 71 and reflected by a mirror 73 onto the inlet cylindrical face of the temporal beam integrator 12. The rotated beam emerging from integrator 12 is passed through expanding lens 20, which is a negative lens for slightly expanding the beam size, thence through spatial beam integrator 25 and onto a mirror 74. The beam reflected by mirror 74 is passed through a collimating lens 75, preferably a plano convex positive lens which reduces the beam size. The beam emanating from collimating lens 75 is directed onto a variable aperture 77, which is preferably a variable diameter iris combined with a variable width slit used to tailor the beam size and profile to a particular ophthalmological surgery procedure, such as a photorefractive keratectomy procedure. The apertured beam from variable aperture 77 is directed onto an imaging lens, preferably a biconvex singlet lens with a focal length of 125 mm. The imaged beam from lens 79 is reflected by a mirror/beam splitter 80 onto the surgical plane 82 at which the apex of the cornea of the patient is positioned. A treatment energy detector 84 senses the transmitted portion of the beam energy at mirror/beam splitter 80. Beam splitter 86 and a microscope objective lens 88 are part of the observation optics. If desired, a video camera may be installed in the optical path of the apertured beam emanating from the microscope objective lens 88 to assist in viewing or recording the surgical procedure. Similarly, a heads-up display may also be inserted in the optical path of the microscope, reflecting from the beam splitter 86 to provide an additional observational capability.

In the application of the invention shown in FIGS. 5A–C, the speed of rotation of the temporal beam integrator is generally dependent upon the nature of the surgical procedure, and is specifically related to the rate at which the laser pulses are generated. In general the rotation rate ranges from about 100 to about 200 revolutions per minute in ophthalmological surgical procedures.

As noted above, cylindrical lenses 13, 14 of temporal beam integrator 12 in the preferred embodiment described above are substantially identical and thus have equal focal lengths. If desired, cylindrical lenses having different focal lengths may be employed as shown in FIG. 6. With reference to this figure, two cylindrical lenses 113, 114 of unequal refractive power are arranged with their axes aligned as shown. Lenses 113, 114 are spaced along the beam axis by a distance equal to the sum of the two focal distances fx, fy. In this embodiment, the size of the laser beam exiting from the exit side of the temporal beam integrator will be affected in width and height by the inverse of the ratio of the first and second integrator lenses 113, 114, and the sine or cosine function of the angle between the entering laser beam and the entrance lens. As will be understood by those skilled in the art, in the FIG. 6 embodiment, either lens 113 or 114 may serve as the entrance lens or the exit lens for the temporal beam integrator. Similarly, it is understood that lenses 113, 114 are arranged and operated in the same manner as that described above with respect to the embodiments of FIGS. 1–5A–C.

The temporal and spatial beam integrator of the invention affords a number of advantages over the known spatial and temporal beam integrator employing the rotating dove prism. Firstly, due to the use of substantially identical cylindrical lenses 13, 14, and the simple mounting arrangement illustrated in FIGS. 3 and 4, the temporal and spatial beam integrator optics can be relatively aligned initially. Further, once aligned, the probability of subsequent misalignment is extremely low. Also, any angular misalignment with respect to the laser beam axis results in a multiplication of the misalignment error on the laser beam by only a factor of approximately 0.5, which compares favorably to an error multiplication factor of 2.0 for a temporal beam integrator using a rotating dove prism.

While the above provides a full and complete disclosure of the preferred embodiments of the invention, various modifications, alternate constructions and equivalents will occur to those skilled in the art. For example, while the invention has been described with express reference to an ophthalmological laser surgery system, other applications of the invention may be made, as desired. Therefore, the above should not be construed as limiting the invention, which is defined by the appended claims.

What is claimed is:

1. A method of processing a collimated laser beam to improve the spatial and temporal characteristics thereof, said method comprising the steps of:

(a) first passing the collimated beam through a temporal beam integrator to rotate the beam about the axis thereof at a predetermined rate; and (b) then passing the rotating beam emerging from the temporal beam integrator through a spatial beam integrator to effect spatial integration thereof.

2. The method of claim 1 wherein said step (a) includes the steps of positioning a pair of cylindrical lenses in spaced relationship along the axis of the collimated beam, and rotating said pair of cylindrical lenses in unison about the beam axis.

3. The method of claim 2 wherein said step of positioning includes the step of spacing said pair of cylindrical lenses along the beam axis by an amount substantially equal to the sum of the focal distances of both cylindrical lenses.

4. The method of claim 3 wherein said cylindrical lenses have substantially equal refractive power.

5. The method of claim 3 wherein said cylindrical lenses have different focal lengths.

6. The method of claim 2 wherein said step (b) includes the step (i) of rotating the spatial beam integrator about the beam axis.

7. The method of claim 6 wherein said step (i) includes the step of rotating the spatial beam integrator at an angular speed greater than the speed of rotation of the cylindrical lenses.

8. The method of claim 7 wherein the angular speed of the spatial beam integrator is twice the speed of rotation of the cylindrical lenses.

9. The method of claim 6 wherein the angular speed of rotation of the spatial beam integrator is equal to the speed of rotation of the cylindrical lenses.

10. The method of claim 1 wherein said step (b) includes the step of maintaining the spatial beam integrator stationary with respect to the rotation of the beam.

11. The method of claim 1 wherein said step (a) is preceded by the step of rotating the spatial beam integrator about the beam axis to initially optimize the spatial characteristics of the collimated beam passing therethrough.

* * * * *